United States Patent [19]

Chima

[11] Patent Number: 4,904,678

[45] Date of Patent: Feb. 27, 1990

[54] SICKLE CELL ANEMIA CONTROL

[75] Inventor: Oji A. Chima, Little Rock, Ark.

[73] Assignee: Jerome J. Norris, Rockville, Md. ; a part interest

[21] Appl. No.: 90,244

[22] Filed: Aug. 25, 1987

[51] Int. Cl.⁴ .................... A61K 31/44; A61K 31/21; A61K 31/26

[52] U.S. Cl. .................................. 514/345; 514/514; 514/515; 514/815

[58] Field of Search ................ 514/815, 515, 514, 345

[56] References Cited

PUBLICATIONS

Raper–*Ann. Soc. Belge Med. Trop.* (1969), 49, 2, 205–210.

*Primary Examiner*—Frederick E. Waddell
*Attorney, Agent, or Firm*—Jerome J. Norris

[57] ABSTRACT

Method of providing anti-sickling of red blood cells in sickle cell anemia patients without hemolyzing said cells, using thiocyanates alone, or together with Vitamin B$_6$.

7 Claims, 5 Drawing Sheets

SICKLE CELL ANEMIA CONTROL

BACKGROUND OF THE INVENTION

Sickle cell anemia is a blood disorder characterized by anemia arising from low levels of hemoglobin and hematocrit (packed red cell volume).

This form of anemia is a hereditary defect resulting from a genetic mutation, wherein a hemoglobin variant (sickle cell) is synthesized instead of the normal adult hemoglobin. In the generic sense, sickle cell disease applies to disorders characterized by human red blood cells, which contain an abnormal hemoglobin, that has been designated hemoglobin S.

When deprived of oxygen, sickle cell hemoglobin becomes insoluble, and forms hemoglobin crystals. These crystals form rigid rods which distort the normally, nearly spherical red blood cells to the sickle shaped forms. It has been found that sickle cells are more fragile than normal red blood cells, and the abnormal shapes of these cells cause them to be easily hemolyzed (broken) in circulating blood.

It has also been found that, in the circulating blood system, the sickled cells are destroyed by the phagocytes of the body's immune system. The rapid loss of the sickled cells leads to low hemoglobin and hematocrit and this precipitates a crisis in the sickle cell patient.

Hemoglobin is the oxygen-carrying protein in the red blood cells, and, in sickle cell anemia, the low hemoglobin, due to the loss of red blood cells, causes an inadequate supply of oxygen for bodily functions. Consequently, in an uncontrolled sickle cell condition, weakness and difficulty in breathing occur, and the sickled cells tend to clog narrow capillaries and cause blood clots which give rise to severe crippling pain in the parts of the body affected.

In the United States, blood transfusions and chemotherapy are the most widely used modes of sickle cell anemia control. In the case of transfusions, unfavorable side effects and risks render it unsafe for long term treatment. For example, in blood transfusion therapy, there are the risks of: transmission of hepatitis; acquired immune deficiency syndrome (AIDS); adverse transfusion reactions; ABO incompatibility; and bacterial contamination.

In the chemotherapy treatment for sickle cell anemia, many of the drugs expose the patient to the risk of toxicity and/or causes the sickled cell to be easily hemolyzed (broken) at the levels of effective usage, or results in other untoward side effects.

It is an object of the present invention to provide a process for effectively clinically treating sickle cell anemia patients without the risks attendant to the complicated process of blood transfusion.

Another object of the invention is to provide a composition for effectively clinically treating sickle cell anemia patients without the risks of toxicity associated with chemotherapy.

A yet further object of the invention is to provide a composition for effectively clinically treating sickle cell anemia patients without the risk of hemolysis or breaking the abnormal cells.

These and other objects of the invention will become more apparent from the invention hereinafter set forth.

SUMMARY OF THE INVENTION

The invention methods of therapy achieves anti-sickling of deoxygenated sickle cell hemoglobin without hemolysis or breaking of the cell, by the use of specified amounts of thiocyanate salts of either alkali metals or ammonium, or these salts together with pyridoxine hydrochloride (vitamin $B_6$).

It has been discovered that when red blood cells taken from a patient suffering from sickle cell anemia are treated with a thiocyanate solution, i.e. sodium, potassium or ammonium thiocyanate at a concentration in amounts from about 20 mM to about 50 mM, these cells are not hemolyzed and are irreversibly prevented from sickling.

When 100 mg. to 500 mg. of potassium thiocyanate in a pharmaceutical tablet or other pharmaceutically acceptable vehicle are administered daily per patient, these cells are not hemolyzed and are irreversibly prevented from sickling.

DETAILED DESCRIPTION OF THE INVENTION

Figure 1:
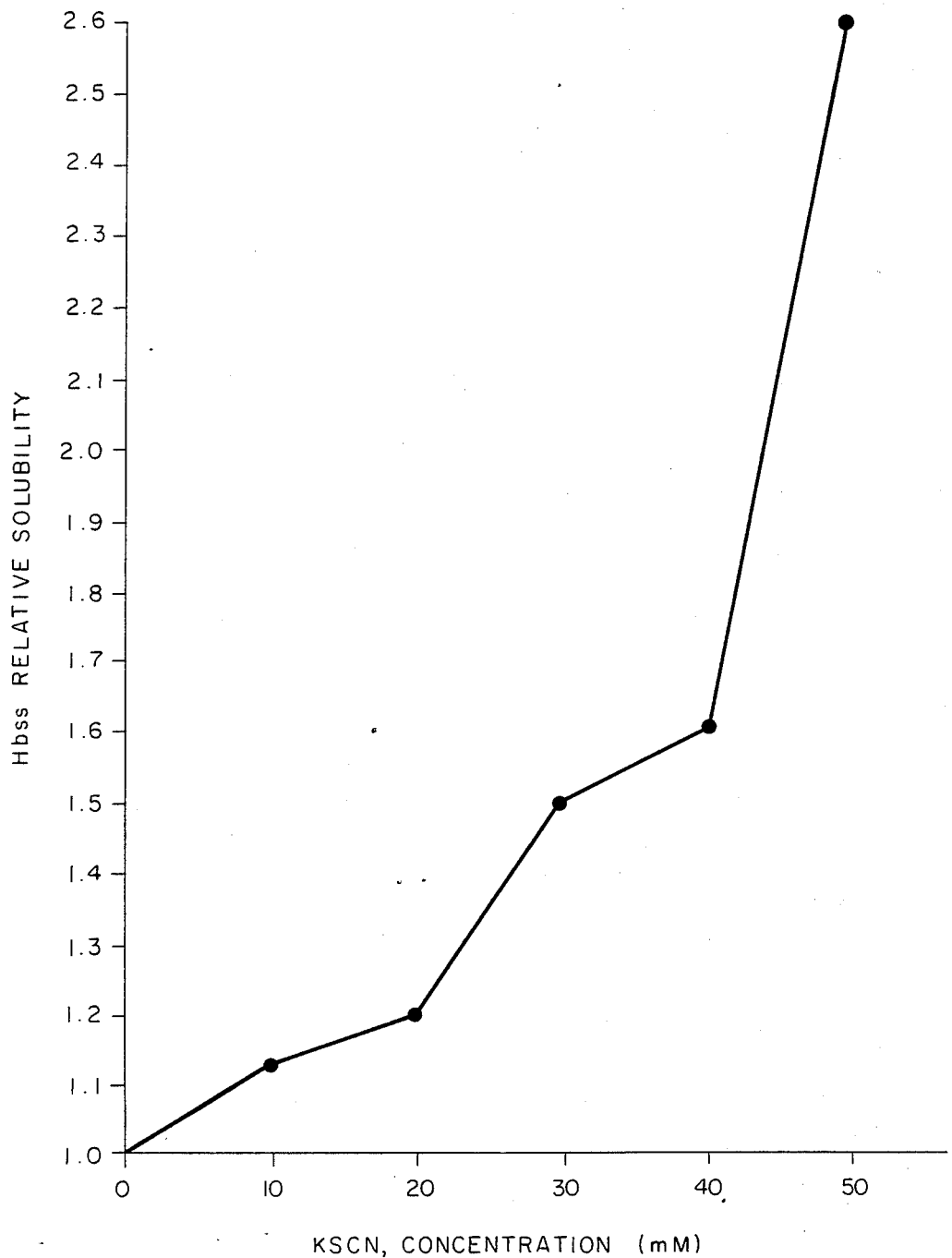

The following description in the practice of this invention was undertaken to investigate the anti-sickling effect of potassium thiocyanate as a representative of the other aforementioned types of thiocyanate. Parameters of erythrocytes with homozygous sickle cell hemoglobin (Hbss-erythrocytes) studied included deoxygenated hemoglobin-S solubility enhancement and morphological evaluation of erythrocytes by scanning electron microscopy. The rationale for selecting these experimental strategies and how they were executed will become apparent in the light of the accompanying disclosure.

The blood samples used in this invention were drawn from sickle cell anemia patients into tubes containing the known anti-coagulant, EDTA. Such tubes prevent the blood from clotting, thereby allowing even distribution of erythrocytes.

To determine the solubility enhancement of deoxygenated sickle cell hemoglobin (Hbss) by potassium thiocyanate, standard solutions of potassium thiocyanate containing 10.0, 20.0, 30.0, 40.0 and 50.0 mM (mM, millimole per liter) respectively were prepared in 0.9% saline solution. A normal saline solution of 0.9% was used as the control. Into small test tubes of $100 \times 13$ mm in dimension, were pipetted 0.5 ml of each thiocyanate standard. This was followed by the addition to each tube, of 0.1 ml of the homozygous sickle cell whole blood sample. The blood sample for each experimental run was uniform (from the same patient). For the control, 0.5 ml of 0.9% saline solution was mixed with 0.1 ml of the whole Hbss blood in the test tube. The blood sample in each tube was mixed gently and manually with potassium thiocyanate and the control saline solution. The reaction tubes were adequately flushed with gaseous nitrogen to deoxygenate the hemoglobin-S, and the tubes were tightly sealed with parafilm. These reaction vessels were incubated for one hour in a waterbath at a temperature of 37 degrees Centigrade. The sealed tubes were allowed to stand at a room temperature of 25 degrees Centigrade for twenty-four hours following the incubation. This step established that the anti-sickling effect of potassium thiocyantate is irreversible within this time.

Separation of Hbss-erythrocytes from the supernatant was achieved by centrifugation of the sample tubes at 1000 g for 20 minutes.

The supernatant was used for the solubility studies, while the erythrocyte sediment was utilized for morphological evaluation of sickle cells by scanning electron microscopy.

For the solubility studies, 0.2 ml of the supernatant from each sample tube were added to 2.0 ml of Drabkin's reagent in the 100×13 mm glass test tube. These tubes were covered with parafilm, and mixed by inversion. They were allowed to stand at room temperature for 10 minutes. The principle behind this method of investigation is that ferricyanide in the Drabkin's reagent converts the ferrous iron atom in hemoglobin to the ferric state. This variant of hemoglobin is believed to react with potassium cyanide, KCN, to form cyanomethemoglobin pigment. About 10 minutes allow these reactions go to completion. Just prior to reading the absorbances, the tubes were inverted gently to obtain a homogenous solution. At a wavelength of 540 nm, the maximum absorbance of cyanometheomglobin, the absorbances of each supernatant were determined and recorded in duplicates.

The effect of potassium thiocyanate on the solubility of deoxygenated hemoglobin-S is expressed as relative solubility ratios. These ratios were obtained by dividing the absorbance of soluble hemoglobin-S in the supernatant of potassium thiocyanate-treated samples by that of the saline control. A higher ratio indicates a higher solubility of deoxygenated hemoglobin-S. Thus, a higher ratio is an index of a better sickling inhibition at the molecular level. This solubility method of evaluating sickling inhibition has been valuable in the evaluation of 15 anti-sickling agents, known and used, see Chang, H. et al, Blood 61 (4): 693–704, (1983). However, the present invention utilized potassium thiocyanate, which was not known or included as an anti-sickling agent in the Chang et al evaluations. Thus, the novelty and uniqueness of the present invention rest on providing a prophylactic or preventive method of sickle cell anemia control based on the demonstration of anti-sickling activity of potassium thiocyanate in certain dose dependent amounts.

Morphological evaluation of potassium thiocyanate-treated cells and controls was executed by means of scanning electron microscopy. The sediments of Hbss-erythrocytes evaluated were taken from the same reaction test tubes used for the hemoglobin-S solubility studies.

In accordance with the invention, the method employed to evaluate the morphology of Hbss erythrocytes by the scanning electron microscopy is as follows.

The Hbss-erythrocyte samples were fixed in 2% glutaraldehyde in 0.1M phosphate buffer. Cells were allowed to attach to the coverslips containing poly-L-lysine and then buffer-rinsed in 0.2M phosphate buffer, and then post-fixed in 1% osmium tetroxide-phosphate buffer. The samples were dehydrated through an ascending grade series of alcohol. The cells were critical point dried in a Tousimis Autosamdri-810. They were then mounted and gold-coated in a Hummer Sputter Coater. Using the JEOL-JSM 35 scanning electron microscope, the Hbss-erythrocytes were viewed at 25 kv (kilovolts) and 15 working distance. The morphologies of the Hbss-erythrocytes in the potassium thiocyanate-treated samples and controls were compared by means of electron micrographs.

Table 1 shows the data derived from deoxygenated hemoglobin-S solubility studies.

TABLE 1

| | Hemoglobin-S Solubility Studies | | |
|---|---|---|---|
| Agent | Concentration | Absorbance (540 nm) $\bar{x}$ | Hbss Relative Solubility Ratio |
| Potassium Thiocyanate | 10 mM | 0.102 | 1.130 |
| | 20 mM | 0.108 | 1.200 |
| | 30 mM | 0.134 | 1.500 |
| | 40 mM | 0.144 | 1.600 |
| | 50 mM | 0.233 | 2.600 |
| Saline | 0.9% | 0.090 | 1.000 |

The graphic representation of relative hemoglobin-S solubility enhancement by potassium thiocyanate is shown in FIG. 1.

Figure 2:
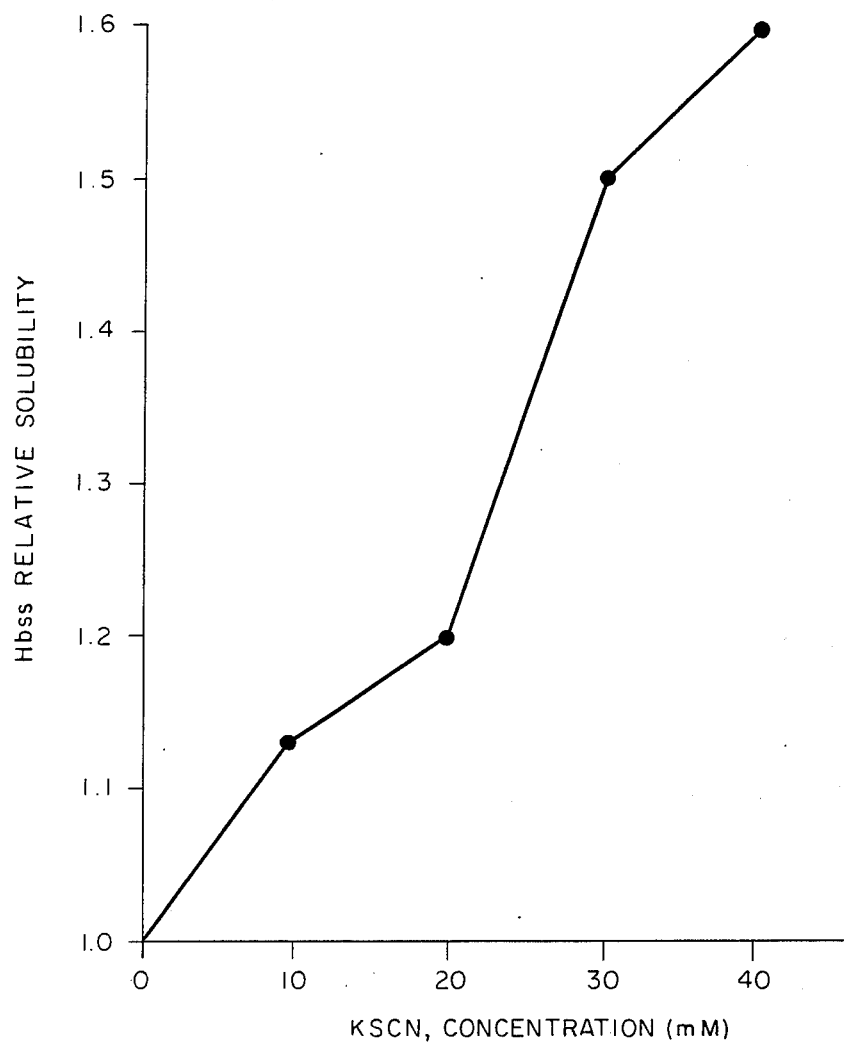

In this graph, Hbss relative solubility is shown at the vertical axis (ordinate) while potassium thiocyanate concentration is given at the horizontal axis (abcissa). FIG. 1 shows a biphasic kinetics of solubility enhancement of deoxygenated hemoglobin-S by potassium thiocyanate. At potassium thiocyanate concentrations of 10.0, 20.0, 30.0 and 40.0 mM the curve displays a sigmoidal kinetics. This concentration range represents the first phase. The second phase is observed from 40.0 to 50.0 mM potassium thiocyanate where the solubility enhancement is greatly increased linearly from 1.6 solubility ratio at 40.0 mM to 2.6 at 50.0 mM. For purpose of clarity, the sigmoidal, first phase is redrawn in FIG. 2.

Within the first phase, or the sigmoidal area of the curve, the potassium thiocyanate concentration range of 20.0 mM to 30.0 mM gives the highest slope. Thus, 20.0 mM represents the minimum, or borderline sickling inhibition concentration, while 30.0 mM potassium thiocyanate exerts a total inhibition of erythrocyte sickling in vitro. A significant increase of deoxygenated hemoglobin-S solubility is achieved at 20.0 to 30.0 mM potassium thiocyanate as shown by the rise of the slope. Data in Chang et al Blood 61 (4): 693–704, (1983), shows that potassium cyanate, KCNO, in a range of 25.0 to 30.0 mM significantly increased the solubility of deoxygenated hemoglobin-S.

The ultimate demonstration of sickling inhibition by potassium thiocyanate is shown by scanning electron microscopy morphological evaluation of Hbss-erythrocytes through the practices of this invention. The ability of potassium thiocyanate to inhibit the morphological alteration of discoid Hbss-erythrocytes to the pathologic, sickle shaped forms is herein shown by the electron photomicrographs. Hbss-erythrocytes with normal, discoid, morphology, if exposed to potassium thiocyanate have normal lifespan. Consequently, anemia in sickle cell patients would get progressively less and less severe as more of their erythrocytes are exposed to potassium thiocyanate in accordance with the practices of the method of treatment herein described.

The experimental embodiment in this invention involved flushing of the reaction test tubes containing the Hbss-erythrocytes with nitrogen gas. This practice was important to create a simulated in vitro spleen. The rationale of this step in this experimental strategy is that Hbss-erythrocytes are usually sickled under the hypoxic environment of the spleen during splenic circulation in vivo. Thus, by experimental manipulation, a similar hypoxic condition was created in vitro which simulates a real life situation. If the Hbss-erythrocytes are inhibited from sickling by potassium thiocyanate in vitro, they will also be inhibited from sickling in vivo through the potassium thiocyanate regimen set forth herein.

Figure 3:
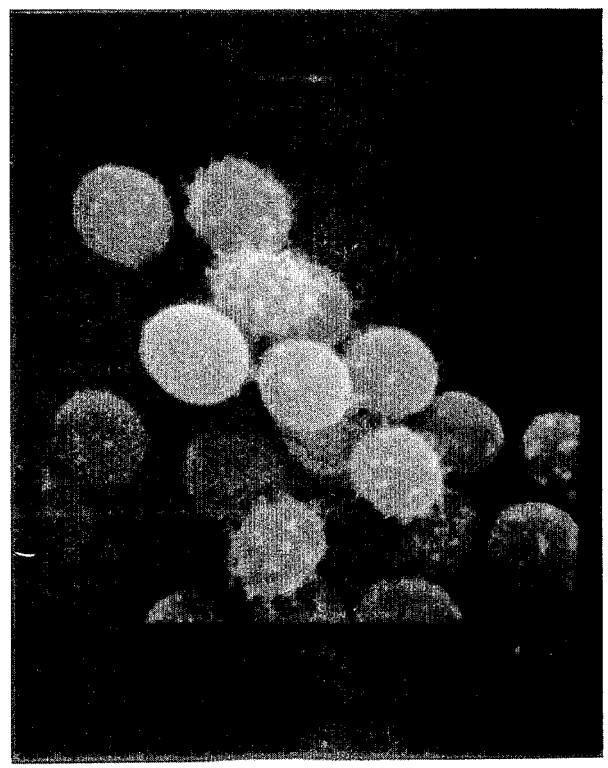

In the scanning electron microscopy study, it is demonstrated that 30.0 mM of potassium thiocyanate totally eliminated sickling in vitro. The electron micrographs are shown in FIG. 3. Normal, discoid morphology of all the Hbss-erythrocytes is maintained. The cells were viewed and photographed at a magnification of 4000×. The morphology result is consistent with the hemoglobin-S solubility data which shows that at 30.0 mM, potassium thiocyanate significantly enhances hemoglobin-S solubility by a factor of 1.5.

The effectiveness and superiority of potassium thiocyanate at this level in sickling inhibition is shown by the electron photomicrograph in FIG. 3.

FIG. 3 shows a scanning electron micrograph of human erythrocytes bearing homozygous sickle cell hemoglobin (Hbss) treated with 30.0 mM of potassium thiocyanate in vitro, and viewed at a magnification of 4000×. Total inhibition of sickling is obvious and normal discoid morphology of erythrocytes is maintained.

In U.S. Pat. No. 3,833,724, it is shown that up to 80% of the erythrocytes are prevented from sickling if about 4 mols of potassium cyanate are incorporated per mol of hemoglobin tetramer; however, in the present invention, potassium thiocyanate at 30.0 mM, has inhibited the sickling of 100% of Hbss-erythrocytes.

The complete elimination of sickling by 30.0 mM of potassium thiocyanate lends support to the epidemiological observation that ingestion of potassium thiocyanate and the incidence and severity of sickle cell anemia are inversely related.

Figure 4:
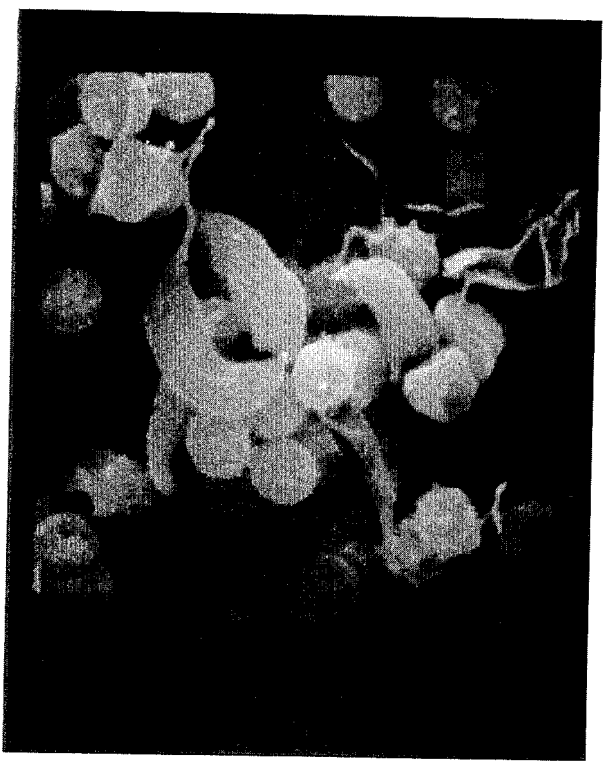

On the other hand, 10.0 mM of potassium thiocyanate failed to inhibit sickling, as shown in the electron micrograph in FIG. 4.

FIG. 4 shows a scanning electron micrograph of human erythrocytes bearing homozygous sickle cell hemoglobin (Hbss) treated in vitro with 10.0 mM of potassium thiocyanate and viewed at a magnification of 4000×. Gross sickling event is evident, showing that, this concentration of potassium thiocyanate failed to inhibit sickling. Thus, it is clear that the anti-sickling activity of potassium thiocyanate is dose-dependent. The Hbss-erythrocytes sickled grossly, and to the same magnitude as in the control sample, treated with only 0.9% saline solution. This data demonstrates that the anti-sickling activity of potassium thiocyanate is dose-dependent. Hence, for effective anti-sickling dosages, potassium thiocyanate must be administered in amounts from about 20.0 mM to about 50.0 mM. This morphology result is consistent with the hemoglobin-S solubility data which showed that 10.0 mM potassium thiocyanate exerts a negligible enhancement of hemoglobin-S solubility. This is evident from the solubility ratio of 1.13 at 10.0 mM, as opposed to 1.5, at 30.0 mM potassium thiocyanate concentration.

The 0.9% saline solution, which served as the control, failed to inhibit sickling.

Figure 5:
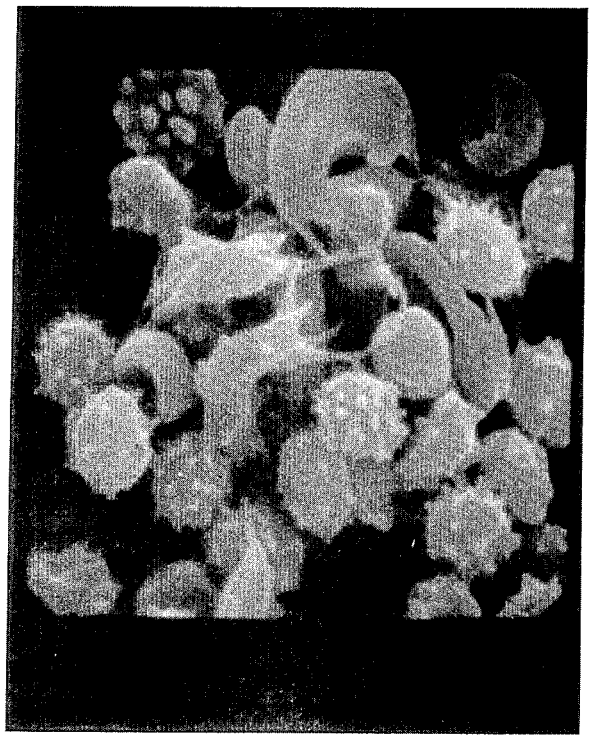

FIG. 5 shows a scanning electron micrograph of human erythrocytes bearing homozygous sickle cell hemoglobin (Hbss) treated in vitro with 0.9% saline, and viewed at a magnification of 4000×. Gross sickling is evident.

It is evident from these results that saline solution has no anti-sickling activity, and 10.0 mM potassium thiocyanate is insufficient to exert any anti-sickling effect in vitro; however, 30.0 mM potassium thiocyanate is effective in exerting 100% sickling inhibition in vitro.

In accordance with the invention, a prophylactic or preventive control of sickle cell anemia and its crisis would be achieved by the administration of potassium thiocyanate or its equivalents such as sodium thicyanate or ammonium thiocyanate to sickle cell patients in amounts from about 100 mg to about 500 mg of these thiocyanates per patient daily. In this regard, about 100 mg to 200 mg of the thiocyanate would be given to patients aged 6 months to 4 years; about 200 mg to 300 mg for patients aged 4 years to 18 years; and about 300 mg to about 500 mg daily to patients above 18 years of age.

Vitamin $B_6$ can be admixed with the thiocyanate, and it is recommended that the proportion of thiocyanate to vitamin $B_6$ be about 20:1. This preparation can be made as one entity. On the other hand, the thiocyanate and vitamin $B_6$ can be administered one after the other as separate components, if desired.

Thiocyanate and thiocyanate admixed with vitamin $B_6$ can be prepared for administration in various forms, such as tablets, solutions, granules, syrups, suppository and other forms known to the drug making technology. In this respect, thiocyanate and pyridoxine hydrochloride (vitamin $B_6$) are both water soluble. Employing the methods of this invention, it was discovered that thiocyanate and vitamin $B_6$ are not antagonistic to each other.

It has been established that vitamin $B_6$ is essential for hemoglobin biosynthesis, and it is known that vitamin $B_6$ is the coenzyme of delta-aminolevulinic acid (ALA) synthetase, the first enzyme in hemoglobin formation in humans, see Hindmarsh, Clin. Chem. 32 (7): 1255–1263, (1986). Therefore, when it is also desirable to prevent depression of hemoglobin biosynthesis arising from Vitamin $b_6$ deficiency, best results are achieved when vitamin $B_6$ is used in combination with potassium thiocyanate. In this way, the thiocyanate-vitamin $B_6$ mode of administration would ensure optimal hemoglobin synthesis and effective prevention of anemia in sickle cell homozygotes.

The routes of administration of the thiocyanate, or thiocyanate-vitamin $B_6$ admixture will mainly include the oral and intravenous modes; however, other modes can also be used. For the prophylactic approach, it has been found that the oral route is the most convenient. For therapeutic control of sickle cell crisis, the oral or the intravenous route could be used. The purpose of the administration is to bring the thiocyanate, or thiocyanate and vitamin $B_6$ in contact with the blood stream. Here, the thiocyanate permeates the erythrocyte membrane, binds to hemoglobin and prevents sickling, and vitamin $B_6$ stimulates hemoglobin biosynthesis.

In the context of the invention, it has been found that alkali metal salts of thiocyanates as well as ammonium thiocyanate are effective to control sickling when used according to the invention; however, the preferred salts are potassium and sodium thiocyanate.

Studies[1,2] have shown that thiocyanates and their dietary precursors, i.e. beta-cyanogenetic glucosides (nitrilosides) are non-toxic and safe for humans, and when these studies are factored into the orbit of the present invention, the evidence suggests that the anti-sickling effect of the thiocyanate observed in vitro corresponds directly to the use of these compounds in vivo, both upon deoxygenated and oxygenated red blood sickle cells (Hbss).

1. Krebs, E. T., Jr. "The Nitrilosides (Vitamin B-17) Their Nature, Occurrence and Metabolic Significance; Antineoplastic Vitamin B-17," Journal of Applied Nutrition 22: 75–86, 1970a.

2. "The Nitrilosides in Plants and Animals," *The Laetriles—Nitrilosides—I The Prevention and Control of Cancer*, McNaughton Foundation, Sausalito, Calif., 1–21, 1970b.

While the emphasis of the invention has been directed to the treatment of those suffering from sickle cell anemia, it is to be understood that the improved results are also obtainable in persons who are sickle cell hemoglobin heterozygotes or suffer from the sickle cell trait.

On the basis of the experiments, the use of thiocyanates according to the invention method can be orally administered as an active ingredient to successfully stop acute sickle cell crises, in amounts ranging from 100 to 500 mg/day. When using the oral administration route, which is the preferred route of the invention, the thiocyanate compound would be admixed with a beverage such as an artificially flavored aqueous beverage or fruit drink. Alternately, a tablet form with an enteric coating can also be used.

Further, in the practice of the invention, red blood cells can be withdrawn from the patient and treated with the thiocyanate solution prior to replacement into the patient. In this procedure of replacement therapy, a portion of the patient's blood is drawn and placed into a vessel containing acid-citrate-dextrose (ACD). The blood is then centrifuged and the plasma is returned to the patient. The red blood cells are incubated with an aqueous solution of the thiocyanate, preferably, potassium thiocyanate (20 mM–50 mM) at about 37 degrees Centigrade for at least an hour. The cells are then washed to remove excess thiocyanate and then re-introduced into the patient.

Intravenous use of a thiocyanate solution, as a sterile physiologically suitable, pyrogen-free sodium thiocyanate solution in amounts from 20 mM to about 50 mM would also appear to inhibit sickling of the red blood cells.

A suppository composition containing the thiocyanate can also be used in administering the thiocyanate, if well known carrier or base materials such as gelatin, glycerinated gelatin, cocoa butter, hydrogenated vegetable oils and mixtures of polyethylene glycols of varying molecular weights and fatty acid esters of polyethylene glycols are made up to melt at internal body temperatures.

What is claimed is:

1. A method of providing anti-sickling of red blood cells in sickle cell anemia patients without hemolyzing the cells comprising, administering in a pharmaceutically acceptable vehicle an anti-sickling, non-hemolyzing amount of thiocyanate selected from the group consisting of alkali metal salts and an ammonium salt until the Hbss relative solubility ratio is at least 1.200 in the deoxygenated hemoglobin-S.

2. The method of claim 1, wherein the alkali metal salts are selected from sodium and potassium.

3. The method of claim 1, wherein ammonium thiocyanate is employed.

4. The method of claim 1, wherein said anti-sickling, non-hemolyzing amount of thiocyanate is admixed with Vitamin $B_6$.

5. The method of claim 2, wherein said sodium and potassium salts of thiocyanate are admixed with Vitamin $B_6$.

6. The method of claim 3, wherein said ammonium thiocyanate is admixed with Vitamin $B_6$.

7. The method of claim 2, wherein said cyanate is used in amounts of from about 100 mg to about 500 mg per patient daily.

* * * * *